(12) United States Patent
Scott et al.

(10) Patent No.: US 7,031,845 B2
(45) Date of Patent: Apr. 18, 2006

(54) METHOD FOR DETERMINING BIOLOGICAL EXPRESSION LEVELS BY LINEAR PROGRAMMING

(75) Inventors: Ridgway Scott, Chicago, IL (US); Stephen J. Wright, Madison, WI (US); Stuart A. Kurtz, Homewood, IL (US); Terry Clark, Chicago, IL (US); Chris (Hristem) Dyanov, Chicago, IL (US); Richard Quigg, Western Springs, IL (US)

(73) Assignee: University of Chicago, Chicago, IL (US)

( * ) Notice: Subject to any disclaimer, the term of this patent is extended or adjusted under 35 U.S.C. 154(b) by 152 days.

(21) Appl. No.: 10/198,141

(22) Filed: Jul. 19, 2002

(65) Prior Publication Data

US 2004/0014044 A1 Jan. 22, 2004

(51) Int. Cl.
*G06G 7/58* (2006.01)
*C12Q 1/68* (2006.01)
*G06N 7/00* (2006.01)

(52) U.S. Cl. ............................. 702/19; 435/6; 702/20; 703/2

(58) Field of Classification Search ...................... 435/6
See application file for complete search history.

(56) References Cited

U.S. PATENT DOCUMENTS 5,695,937 A * 12/1997 Kinzler et al. .................. 435/6
6,344,316 B1 * 2/2002 Lockhart et al. ............... 435/6
2002/0012926 A1 * 1/2002 Quake et al. ................... 435/6

OTHER PUBLICATIONS

Holter, et al., Dynamic modeling of gene expression data, PNAS, 98(4):1693-98 (2001).*
Brown, et. al., Knowledge-based analysis of microarray gene expression data by using support vector machines, PNAS, 97(1):262-67 (2000).*
Hu, et. al., Predicting Splice Variant from DNA Chip Expression Data, Genome Research, 11:1237-45 (2001).*
Bras, M., Cloarec, J., Bessueille, F., Souteyrand, E., Martin, J., and Chauvet, J. Control of immobilization and hybridization on DNA chips by fluorescence spectroscopy. *Journal of Fluorescence* 10 (2000), 247-253.
Clark, T., Lee, S., Scott, L. R., and Wang, S. M. Computational analysis of gene identification with SAGE. *J. Comp. Bio.*, accepted.
Hernaiz, M., Liu, J., Rosenberg, R., and Linhardt, R. Enzymatic modification of heparan sulfate on a biochip promotes its interaction with antithrombin iii. *Biochemical and Biophysical Research Communications* 276 (2000), 292-297.
Kane, M. D., Jatkoe, T. A., Stumpf, C. R., Lu, J., Thomas, J.D., and Madore, S. J. Assessment of the sensitivity and specificity of oligonucleotide (50mer) arrays. *Nuclei Acids Research* 28, 22 (2000), 4552-4557.
Li, C., and Wong, W. H. Model-based analysis of oligonecleotide arrays: expression index computation and outlier detection. *Proc. Natl. Acad. Sci. U.S.A.* 98 (2001), 31-36.
Li, C., and Wong, W. H. Model-based analysis of oligonecleotide arrays: model validation, design issues and standard error application. *Genome Biology* 2 (2001), 32.1-32.11.
Lipshutz, R. J., Fodor, S. P. A., Gingeras, T. R., and Lockhart, D. J. High density synthetic oligonucleotide arays. *Nature Genetics* 21 (1999), 20-24.

(Continued)

*Primary Examiner*—Marjorie A. Moran
*Assistant Examiner*—Marina Miller
(74) *Attorney, Agent, or Firm*—Oblon, Spivak, McClelland, Maier & Neustadt, P.C.

(57) ABSTRACT

A method for determining a matrix of expression levels corresponding to a set of biological targets (e.g., genes or gene fragments) and a set of biological samples, including obtaining a matrix of signal values corresponding to the set of biological targets; computing a vector of expression levels for a sample in the set of biological samples using the matrix of signal values; storing the vector of computed expression levels in a storage matrix; repeating the computing and storing steps for each sample in the set of biological samples; and outputting the storage matrix as the matrix of expression levels. The method, based on a linear programming formulation of the problem, works for both "promiscuous" probe array data, in which there may be multiple targets indicated by a single probe, and the "polygamous" case, in which there are multiple probes for a single target. The preferred method can also process data obtained from multiple SAGE analyses using multiple markers. A second embodiment of the method determines optimal expression levels when the available probe data is noisy or uncertain.

17 Claims, 3 Drawing Sheets

OTHER PUBLICATIONS

Lueking, A., Horn, M., Eickhoff, H., Bussow, K., Lehrach, H., and Walter, G. Protein microarrays for gene expression and antibody screening. *Analytical Biochemistry* 270 (1999), 103-111.

Macbeath, G., Koehler, A. N., and Schreiber, S. L. Printing small molecules as microarrays and detecting protein-ligand interactions en masse. *J. Am. Chem. Soc.* 121 (1999), 7967-7968.

Macbeath, G., and Schreiber, S. L. Printing proteins as microarrays for high-throughput function determination. *Science* 289, 5485 (2000), 1760-1763.

Walter, et al., S. L. Protein arrays for gene expression and molecular interaction screening. *Curr. Opin. Microbiol.* 3 (2000). 298-302.

Peyret, N., Seneviratne, P.A., Allawi, H. T., and Santalucia, Jr., J. Nearest-neighbor thermodynamics and NMR of DNA sequences with A-A, C-C, G-G, and T-T mismatches. *Biochemistry* 38 (1999), 3468-3477.

Pilarsky, C. P., Schmitt, A. O., Dahl, E., and Rosenthal, A. Microarrays—chances and challenges. *Curr. Opin. Molecular Therapeutics* 1 (1999), 727-737.

Schena, M., Shalon, D., Davis, R. W., and Brown, P.O. Quantitative monitoring of gene expression patterns with a complementary DNA microarray. *Science* 270 (1995), 467-470.

Uetz, P., Giot, L., Cagney, G., Mansfield, T. A., Judson, R.S., Knight, J.R., Lockshon, D., Narayan, V., Srinivasan, M., Pochart, P., Qureshi-Emili, A., Li, Y., Godwin, B., Conover, D., Kalbfleisch, T., Vijayadamodar, G., Yang, M., Johnston, M., Fields, S., and Rothberg, J. M. A comprehensive analysis of protein-protein interactions in *Saccharomyces cerevisiae*. *Nature* 403 (2000), 623-627.

Vo-Dinh, T., and Cullum, B. Biosensors and biochips: advances in biological and medical diagnostics. *Fresenius Journal of Analytical Chemistry* 366 (2000), 540-551.

Warrington, J.A., Dee, S., and Trulson, M. Large-scale genomic analysis Affymetrix GeneChip (R) probe arrays. In *Microarray biochip technology*. Eaton Publishing, 2000, pp. 119-148.

Wright, G., Cazares, L., Leung, S., Nasim, S., Adam, B., Yip, T., Schellhammer, P.F., Gong, L., and Vlahou, A. Proteinchip(R) surface enhanced laser desorption/ionization (SELDI) mass spectrometry: a novel protein biochip technology for detection of prostate cancer biomarkers in complex protein mixtures screening. *Prostate Cancer and Prostatic Diseases* 2 (1999). 264-276.

Yershov, G., Barsky, V., Belgovskiy, A., Kirillov, E., Kreindlin, E., Ivanov, I., Parinov, S., Guschin, D., Drobishev, A., Dubiley, S., and Mirzabekov, A. DNA analysis and diagnostics on oligonucleotide microchips. *Proc. Natl. Acad.Sci. U.S.A.* 93 (1996), 4913-4918.

Lee, S., Clark, T., Chen, J., Zhou, G., Scott, L.R., Rowley, J.D., and Wang S.M. Correct Identification of Genes from Serial Analysis of Gene Expression Tag Sequences. *GENOMICS* vol. 79, No. 4, (Apr. 2002), 598-602.

Schreiber, S.L., Protein Chips Offer Powerful Method for Probing Protein Function, (Sep. 2000), pp. 1-3.

Van Dam, R.M., and Quake, S.R. Gene Expression Analysis with Universal n-mer Arrays. *Cold Spring Harbor Laboratory Press ISSN.* (2002), 145-152.

Zhang, L., Zhou, W., Velculescu, V.E., Kern, S.E., Hruban, R.H., Hamilton, S.R., Vogelstein, B., and Kinzler, K.W. Gene expression profiles in normal and cancer cells. *Science* 276 (1997) 1268-1272.

\* cited by examiner

SEQUENCE LISTING

<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: synthetic polynucleotide

<400> SEQUENCE: 1
catgaaccgg ttaa                                                                14

<210> SEQ ID NO 2
<211> LENGTH: 14
<212> TYPE: DNA
<213> ORGANISM: Artificial Sequence
<220> FEATURE:
<223> OTHER INFORMATION: synthetic polynucleotide

<400> SEQUENCE: 2
ctagaaccgg ttaa                                                                14

METHOD FOR DETERMINING BIOLOGICAL EXPRESSION LEVELS BY LINEAR PROGRAMMING

BACKGROUND OF THE INVENTION

Field of the Invention

The present invention relates generally to systems and methods for the determination of biological expression levels present in a biological sample using data obtained from biological expression arrays.

The present invention includes the use of various technologies described in the references identified in the following LIST OF REFERENCES by the author(s) and year of publication and cross-referenced throughout the specification by reference to the respective number, in parentheses, of the reference:

LIST OF REFERENCES

[1] BERTSEKAS, D. P. *Nonlinear Programming, $2^{nd}$ Edition*. Athena Scientific, 1999.
[2] BRAS, M., CLOAREC, J., BESSUEILLE, F., SOUTEYRAND, E., MARTIN, J., AND CHAUVET, J. Control of immobilization and hybridization on DNA chips by fluorescence spectroscopy. *Journal of Fluorescence* 10 (2000), 247–253.
[3] CANTOR, C. R., AND SMITH, C. L. *Genomics*. Wiley, 1999.
[4] CLARK, T., LEE, S., SCOTT, L. R., AND WANG, S. M. Computational analysis of gene identification with SAGE. *J. Comp. Bio.*, accepted.
[5] HERNAIZ, M., LIU, J., ROSENBERG, R., AND LINHARDT, R. Enzymatic modification of heparan sulfate on a biochip promotes its interaction with antithrombin iii. *Biochemical and Biophysical Research Communications* 276 (2000), 292–297.
[6] KANE, M. D., JATKOE, T. A., STUMPF, C. R., LU, J., THOMAS, J. D., AND MADORE, S. J. Assessment of the sensitivity and specificity of oligonucleotide (50 mer) arrays. *Nuclei Acids Research* 28, 22 (2000), 4552–4557.
[7] LI, C., AND WONG, W. H. Model-based analysis of oligonucleotide arrays: expression index computation and outlier detection. *Proc. Natl. Acad. Sci. U.S.A.* 98 (2001), 31–36.
[8] LI, C., AND WONG, W. H. Model-based analysis of oligonucleotide arrays: model validation, design issues and standard error application. *Genome Biology* 2 (2001), 32.1–32.11
[9] LIPSHUTZ, R. J., FODOR, S. P. A., GINGERAS, T. R., AND LOCKHART, D. J. High density synthetic oligonucleotide arrays. *Nature Genetics* 21 (1999), 20–24.
[10] LUEKING, A., HORN, M., EICKHOFF, H., BUSSOW, K., LEHRACH, H., AND WALTER, G. Protein microarrays for gene expression and antibody screening. *Analytical Biochemistry* 270 (1999), 103–111.
[11] MACBEATH, G., KOEHLER, A. N., AND SCHREIBER, S. L. Printing small molecules as microarrays and detecting protein-ligand interactions en masse. *J. Am. Chem. Soc.* 121 (1999), 7967–7968.
[12] MACBEATH, G., AND SCHREIBER, S. L., Printing proteins as microarrays for high-throughput function determination. *Science* 289, 5485 (2000), 1760–1763.
[13] Walter, et al., S. L. Protein arrays for gene expression and molecular interaction screening. *Curr. Opin. Microbiol.* 3 (2000), 298–302.
[14] MARK SCHENA, E. *Microarray biochip technology*. Eaton Publishing, 2000.
[15] NOCEDAL, J., AND WRIGHT, S. J. *Numerical optimization*. Springer, 1999.
[16] PEYRET, N., SENEVIRATNE, P. A., ALLAWI, H. T., AND SANTALUCIA, JR., J. Nearest-neighbor thermodynamics and NMR of DNA sequences with A-A, C-C, G-G, and T-T mismatches. *Biochemistry* 38 (1999), 3468–3477.
[17] PILARSKY, C. P., SCHMITT, A. O., DAHL, E., AND ROSENTHAL, A. Microarrays—chances and challenges. *Curr. Opin. Molecular Therapeutics* 1 (1999), 727–737.
[18] SCHENA, M., SHALON, D., DAVIS, R. W., AND BROWN, P. O. Quantitative monitoring of gene expression patterns with a complementary DNA microarray. *Science* 270 (1995), 467–470.
[19] UETZ, P., GIOT, L., CAGNEY, G., MANSFIELD, T. A., JUDSON, R. S., KNIGHT, J. R., LOCKSHON, D., NARAYAN, V., SRINIVASAN, M., POCHART, P., QURESHI-EMILI, A., LI, Y., GODWIN, B., CONOVER, D., KALBFLEISCH, T., VIJAYADAMODAR, G., YANG, M., JOHNSTON, M., FIELDS, S., AND ROTHBERG, J. M. A comprehensive analysis of protein-protein interactions in *Saccharomyces cerevisiae*. *Nature* 403 (2000), 623–627.
[20] VO-DINH, T., AND CULLUM, B. Biosensors and biochips: advances in biological and medical diagnostics. *Fresenius Journal of Analytical Chemistry* 366 (2000), 540–551.
[21] WARRINGTON, J. A., DEE, S., AND TRULSON, M. Large-scale genomic analysis Affymetrix GeneChip (R) probe arrays. In *Microarray biochip technology*. Eaton Publishing, 2000, pp. 119–148.
[22] WRIGHT, G., CAZARES, L., LEUNG, S., NASIM, S., ADAM, B., YIP, T., SCHELLHAMMER, P. F., GONG, L., AND VLAHOU, A. Proteinchip(R) surface enhanced laser desorption/ionization (SELDI) mass spectrometry: a novel protein biochip technology for detection of prostate cancer biomarkers in complex protein mixtures screening. *Prostate Cancer and Prostatic Diseases* 2 (1999), 264–276.
[23] YERSHOV, G., BARSKY, V., BELGOVSKIY, A., KIRILLOV, E., KREINDLIN, E., IVANOV, I., PARINOV, S., GUSCHIN, D., DROBISHEV, A., DUBILEY, S., AND MIRZABEKOV, A. DNA analysis and diagnostics on oligonucleotide microchips. *Proc. Natl. Acad. Sci. U.S.A.* 93 (1996), 4913–4918.
[24] LEE, S., CLARK, T., CHEN, J., ZHOU, G., SCOTT, L. R., ROWLEY, J. D., AND WANG S. M. Correct Identification of Genes from Serial Analysis of Gene Expression Tag Sequences. *GENOMICS Vol.* 79. Number 4, (April 2002), 598–602.
[25] SAGEMAP: SERIAL ANALYSIS OF GENE EXPRESSION TAG TO GENE MAPPING. National Center for Biotechnology Information (NCBI).
[26] VAN DAM, R. M., AND QUAKE, S. R. Gene Expression Analysis with Universal n-mer Arrays, *Cold Spring Harbor Laboratory Press ISSN.* (2002), 145–152.
[27] ZHANG, L., ZHOU, W., VELCULESCU, V. E., KERN, S. E., HRUBAN, R. H., HAMILTON, S. R., VOGELSTEIN, B., AND KINZLER, K. W. Gene expression profiles in normal and cancer cells, *Science* 276 (1997), 1268–1272.

The entire contents of each reference listed in the LIST OF REFERENCES, are incorporated herein by reference.

DISCUSSION OF THE BACKGROUND

Biological expression arrays are introducing a type of massively parallel processing in experimental biology and medicine [17][20]. Gene expression arrays based on cDNA's [18] and on oligonucleotides [21] have reached a level in which the technology is well established, with books devoted to the subject [14]. Current research includes efforts to refine the technology [2].

More recently, protein expression arrays have been developed [12][13][22][19], and utilized to identify antibodies [10]. Other examples of biological expression arrays include small molecule expression arrays [11] as well as other specialized arrays [5].

Biological expression arrays are arrays of small biochemical experiments, each of which can be different from the other. Each "dot" on the array contains a reactant, called a probe. The set of all probes can be tested against a sample, which presumably contains a set of so-called targets which are to be determined, together with their quantity, or "expression level." For gene expression arrays, the targets are genes or gene fragments (called expressed sequence tags, or ESTs). The "expression levels" could as well be ratios of other more basic quantities, such as the ratio of the observed value for a perfect match and a mismatch [7][8].

The process of matching probes and targets for gene expression arrays is called hybridization. If the hybridization is perfect complementarity, the product may rather be called a perfect complement rather than a hybrid. But when there are some complementarity mismatches, as is the general case, it is appropriate to think of the probe and target as coming from different genes, so the word hybrid is more appropriate. There is a difference between levels or detection signals of hybridization values (the input data) and expression values (the desired answer). In some cases, these are in a one-to-one relationship, so both are often called "expression" values, but in general they are not related in a simple way.

Arrays based on oligonucleotide probes of various lengths have been widely (often) used. A string of n bases is referred to as an n-mer. In the literature, one finds data from using 8-mers [23], 25-mers [21], 50-mers [6], and even longer oligonucleotides probes are currently in use as discussed on web sites. DNA-arrays based on probes consisting of significantly longer sequences (a few hundred bases) when synthesized via template-dependent enzymatic reactions are often called cDNA arrays [18]. A positive hybridization signal from the array is assumed to mean a complementary match (or near match) of sequences between the targets and the probes.

One successful approach to gene expression determination is that adopted by Affymetrix, Inc. (Santa Clara, Calif.) [21]. In their technique, oligonucleotides from several parts (loci) of a known gene are used to define array probes. This redundancy insures a high degree of certainty in identifying the expression of that gene, allowing precise discriminative detection between perfect matching and mismatching of probes to hybrids. (One presumes that care is also taken to be sure that the resulting oligonucleotides are unique and do not also appear in other relevant, either known or unknown genes or ESTs, which, in general, is impossible to be absolutely certain about.) For each perfect-match probe, a "mis-match-probe" is used which differs from the perfect-match probe by one single base, typically chosen in the middle of the oligonucleotide. Thus there should be an expected relation [3][16] between the expression level for a perfect-match complementary probe and its corresponding mis-match-probe. If these conditions are met for most, or many, of the probes for a given gene, it is highly likely that gene has been expressed.

A drawback to this approach is that multiple probes are required to determine a given gene. This approach is considered "polygamous" in that there are multiple probes presented on the array for a single target detection. When the expected relationship between the hybridization levels detected for a probe and its corresponding mis-match-probe are not met, the data for these probes is regarded as noise. There are many potential causes of such "noise" in expression data. For example, if some genetic contaminant is present that complementary matches exactly the mis-match-probe, the corresponding expression level for the "probe" (i.e., the perfect-match probe) would be of a "mis-match" level, inverting the signal ratio.

It would be advantageous to allow for more complex scenarios in which all of the discrete probe data is used for expression determination, rather than segregating them into groups and thus limiting the data from a group of discrete values to single-valued indications for a particular gene. This approach would also reduce the need for the probes to be "unique" markers for particular genes.

It could be possible to interrogate more genes even than the number of available probes, although this would not be possible if all genes were present in a given experiment. This would be done by having a particular probe to indicate the presence of multiple targets, albeit ambiguously. The new approach is "promiscuous" in that a single probe can indicate presence of multiple targets. In the promiscuous approach, all hybridization data becomes valuable signal. Complex hybridization scenarios (e.g., multiple-base mismatches) can (potentially) be included productively in the array hybridization data (signal) analysis.

Serial Analysis of Gene Expression, or SAGE™, is a technique designed to take advantage of high-throughput sequencing technology to obtain a quantitative profile of cellular gene expression [24][27][25][4]. A more detailed description of SAGE is given in U.S. Pat. No. 5,695,937, the entire contents of which are incorporated herein by reference. SAGE allows for the simultaneous quantitative analysis of a large number of mRNA transcripts. The SAGE method has two steps. First, short sequence tags (10–14 bp) are generated from the mRNA. Each tag should contain sufficient information to identify a unique transcript, provided that the tag is derived from a defined location within that transcript. Second, transcript tags are concatenated into a single molecule and then sequenced, revealing the identity of multiple tags simultaneously. The expression pattern of any population of transcripts can be quantitatively evaluated by determining the abundance of individual tags and identifying the gene corresponding to such a tag. The data produced by the SAGE method is a list of tags, with their corresponding count values, and can be portrayed as a digital representation of cellular gene expression.

SUMMARY OF THE INVENTION

Accordingly, it is an object of the present invention to provide a method and computer program product for determining biological expression levels from complex, "promiscuous" array hybridization data that also works well in the "polygamous" case.

Another object of the present invention is to provide a method and computer program product for determining biological expression levels from data derived from SAGE analysis.

Another object of the present invention is to provide a method and computer program product for determining biological expression levels from uncertain or noisy probe array hybridization data.

The above and other objects are achieved according to the present invention by providing a method for determining a matrix of expression levels corresponding to a set of biological targets and a set of biological samples, including obtaining a matrix of signal values P corresponding to the set of biological targets; computing a vector of expression levels for a sample in the set of biological samples using the matrix of signal values P; storing the vector of expression levels computed in the computing step in a storage matrix; repeating the computing and storing steps for each sample in the set of biological samples; and outputting the storage matrix as the matrix of expression levels.

According to this method, the computing step includes obtaining a vector of signal values A corresponding to the sample; determining a nonnegative vector E, a nonnegative vector s, and a nonnegative vector t that minimize a total sum of all elements of s and t, and satisfy a constraint PE+s−t=A; and setting the vector of expression levels to be the nonnegative vector E determined in the determining step.

In addition, further steps are provided for computing the vector of expression levels when the signal data is uncertain or noisy, including obtaining a vector of lower signal values L and a vector of higher signal values H corresponding to the sample, each element of L being less than or equal to a respective element of H; determining a nonnegative vector E, a nonnegative vector s, and a nonnegative vector t, that minimize a total sum of all elements of s and t, and satisfy constraints $s \geq L-PE$ and $t \geq PE-H$; and setting the vector of expression levels to be the nonnegative vector E determined in the determining step.

An important aspect of the present invention is the formulation of the biological expression determination problem as a problem that can be solved using linear programming techniques.

Further, methods are provided for expression identification. In this problem, a particular target g gives rise to a certain array of signal values P(g). Suppose a set U denotes a "universe" of targets. In any expression array experiment, some set of targets S, which is a subset of U, will be active, and are to be identified.

To that end, according to an aspect of the present invention, there is provided a method for identifying a set of biological targets S=S(A) consistent with a vector of nonnegative signal values A, wherein the array P(g) is compared to the vector A, for each target g in the set of universal targets U.

According to another aspect of the present invention, there is further provided a method for computing a multiplicity vector D(A) that corresponds to the vector of nonnegative signal values A. Each element of D(A) indicates the number of targets with a nonnegative signal value in the corresponding position in P(g). This method makes use of the set S(A) to compute the multiplicity vector D(A).

According to another aspect of the present invention, there is further provided a method for identifying the subset of ambiguous targets ΔS(A) that may be expressed in a vector of nonnegative signal values A, but cannot be identified with certainty. This method makes use of both the set S(A) and the multiplicity vector D(A).

According to another aspect of the present invention, there is further provided a method for identifying the set of uniquely expressed biological targets S(A)\ΔS(A) represented by a vector of nonnegative signal values A. This set consists of those targets in S(A) that are not in the set ΔS(A).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
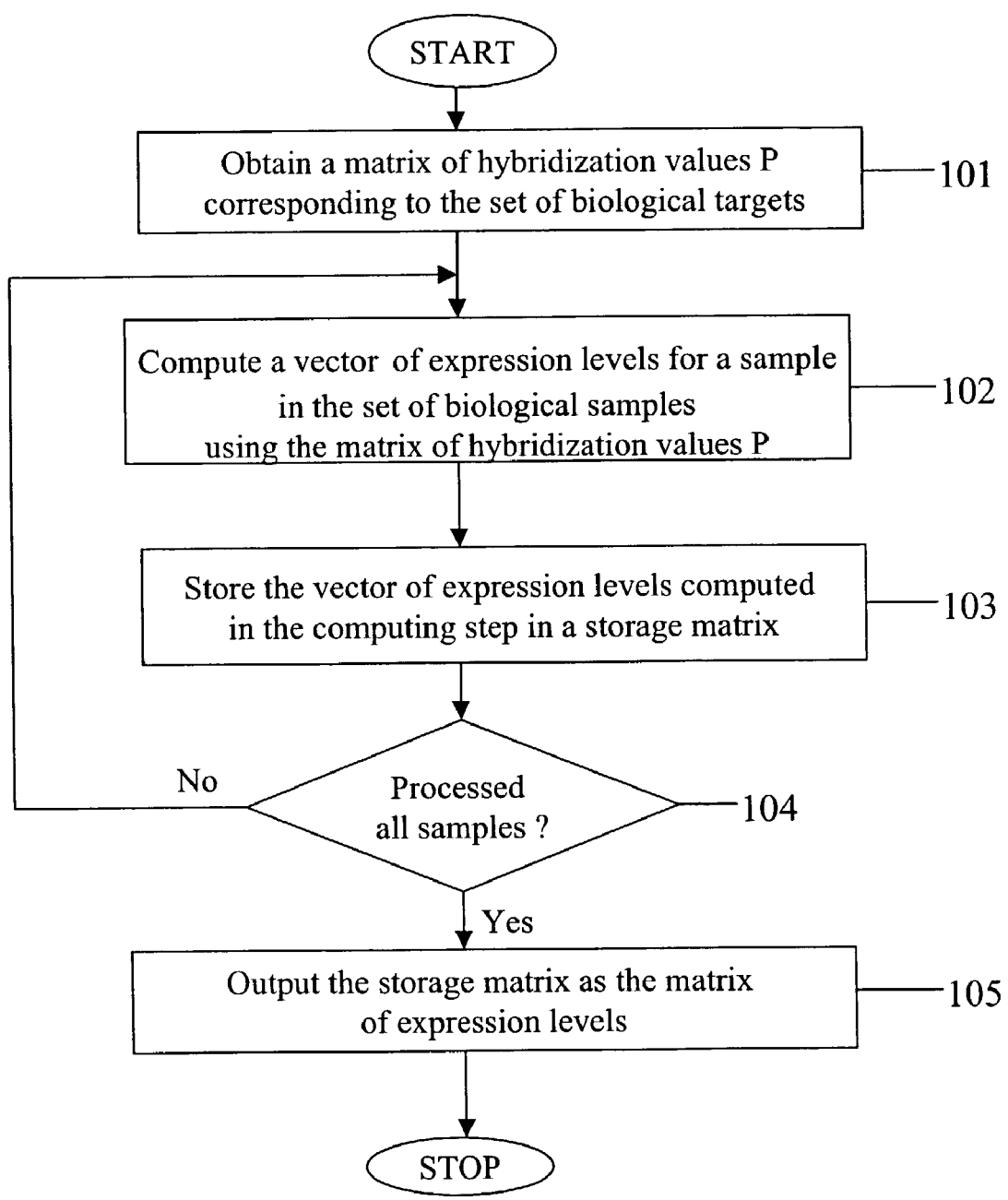
FIG. 1 is a flowchart showing the steps of determining a matrix of biological expression levels corresponding to a set of biological targets and a set of biological samples according to a first embodiment of the present invention.

Biological arrays have as their digital output an array $A=(A_l)$ of hybridization values. Even though these often appear in a two dimensional array, it is assumed they are numbered by a single index l. A typical size array today has from a few thousand to as many as three-hundred thousand cells, and this could be expected to grow in the future, up to a million cells [9].

In a simplified model, these values are either zero or one (expressed or non-expressed: this might be achieved by thresholding real hybridization values). If such a determination could be made unambiguously, it would provide useful answers to biological questions. At the moment, even this is not a simple matter from a practical point of view. What is the mathematical structure of such a problem? In such a simplified system, particular targets g would cause a certain hybridization array P(g) to occur. P(g) is an array of hybridization levels, but again we can think initially of these as being either zero or one. This simplification of hybridization levels is sufficient to define the identification problem.

To begin with, assume that there is a set U of targets that denotes a "universe" of targets. The true "universe" may not be completely known at the moment, e.g., for gene expression arrays, since not all genes have been identified. But it is important to have this set as an underlying concept. In any expression-array experiment, some set S of targets that is a subset of U will be active, and it is this set that we want to identify. If, for some reason, it is known that the size of U can be restricted in a given experiment, then that can be done. The data from the experiment will be a particular hybridization array A of values of zero or one for each given probe. The identification problem can then be described as follows:

Determine the set $S \subset U$ of targets defined by $$S=S(A)=\{g \in U : P(g) \leq A\} \qquad (1)$$

where for two arrays A and B we say $B \leq A$ if $A_l$ is one whenever $B_l$ is one (equivalently $B_l \leq A_l$ for all l).

For the human genome, the size of U is expected to be about one-hundred thousand ($10^5$). It is harder to predict the expected size of a typical S, but an estimate of $10^3$ to $10^4$ might be reasonable.

A solution S(A) to (1) can be computed by the following algorithm.

Algorithm 1 Loop over all $g \in U$ and test whether or not $P(g) \leq A$. If it is, include g in S(A).

Each test $P(g) \leq A$ requires a number of operations proportional to the number of non-zeros in P(g). Thus we have the following result.

Theorem 1 Algorithm 1 finds a solution to equation (1) in an amount of time that is linearly proportional to the size of the universe of targets U, and the constant of proportionality depends only on the average number of non-zeroes in any P(g).

The notion of P(g) can be generalized to apply to a set: $P(S)_l = 1$ if $P(g)_l = 1$ for some $g \in S$, and $P(S)_l = 0$ if $P(g)_l = 0$ for all $g \in S$. Note that for any array A and any set $S \subset U$, we have $P(S) \leq A$ if and only if $P(g) \leq A$ for all $g \in S$. In general, if $R \subset S$ then $P(R) \leq P(S)$.

Algorithm 1 always constructs S(A) so that $P(S(A)) \leq A$. One difficulty that can arise is that $P(S(A)) \neq A$. If this occurs, either there was an error in the experiment, or there was a target that was not represented in U. However, the following theorem says that the set S(A) constructed in Algorithm 1 is the largest solution to the identification problem.

Theorem 2. Suppose there is a set $R \subset U$ such that $P(R) \leq A$. Then $R \subset S(A)$.

Proof: Suppose that $g \in R$. Since $P(R) \leq A$, we have $P(g) \leq A$. Hence by definition $g \in S(A)$.

Another problem can arise due to a kind of non-uniqueness. It may be that there are smaller sets $R \subset S$ such that $P(R) = P(S)$. Any targets in the difference $S \setminus R$ are possibly being expressed, but they cannot be identified for sure. However, it is possible to quantify the amount of non-uniqueness, as follows.

In constructing S(A), it is possible to keep track of the multiplicity of each array point l, by which we mean the number of times this point had a non-zero value in P(g) for some $g \in S(A)$. This defines an array D(A) of such values, as follows:

$$D(A)_l = \text{cardinality}\{g \in S(A) : P(g)_l = 1\}. \quad (2)$$

Given an array D(A) of degree values for S(A) define $D(A)^-$ to be the array obtained from D(A) by decrementing each positive array value. Thus the non-zero array values in $D(A)^-$ correspond to array values in D(A) that were two or more, that is, ones that are multiply expressed. Now define $$\Delta S(A) = \{g \in S(A) : P(g) \leq D(A)^-\}. \quad (3)$$

Lemma 1 For any $g \in S(A) \setminus \Delta S(A)$ there is at least one array index $l_g$ such that $P(g)_{l_g} = 1$ and for all other $g' \in S(A)$ (with $g \neq g'$) we have $P(g')_{l_g} = 0$.

Proof: For a given $g \in S(A)$, let $l_1, \ldots, l_k$ enumerate all of the array indices such that $P(g)_{l_i} = 1$; $k \geq 1$ by the definition of S(A). In particular, this means that $D(A)_{l_i} \geq 1$ for $i = 1, \ldots, k$. If the degree of $l_i$ is more than one for all i (i.e., $D(A)_{l_i} \geq 2$ for $i = 1, \ldots, k$), then $g \in \Delta S(A)$. If $g \in S(A) \setminus \Delta S(A)$, then for one of the i's, it must be true that $D(A)_{l_i} = 1$, and this means that for no other $g' \in S(A)$ can $P(g')_{l_i} = 1$.

Theorem 3 For any array A and for any set $R \subset U$ such that $P(R) = P(S(A))$, then $S(A) \setminus \Delta S(A) \subset R$.

Proof: To begin with, Theorem 2 implies that it can be assumed that $R \subset S(A)$. By Lemma 1, if $g \in S(A) \setminus \Delta S(A)$ then there is an index $l_g$ such that $P(g)_{l_g} = 1$ and $P(g')_{l_g} = 0$ for all $g' \in S(A)$ with $g \neq g'$, and a fortiori for all $g \neq g' \in R$.

If $g \notin R$, then $P(g')_{l_g} = 0$ for all $g' \in R$. This would imply that $P(R)_{l_g} = 0$. By Theorem 2, $P(S(A) \setminus \Delta S(A)) \leq P(S(A))$. Since $P(g)_{l_g} = 1$ implies $P(S(A) \setminus \Delta S(A))_{l_g} = 1$, it must be true that $P(R)_{l_g} = P(S(A))_{l_g} = 1$ by assumption. Since this would be a contradiction, it must be true that $g \in R$.

Corollary 1 S(A) is the largest possible set of expressed targets consistent with a hybridization array A. $S(A) \setminus \Delta S(A)$ is the largest set of uniquely expressed targets represented by A. $\Delta S(A)$ contains all the ambiguous targets which may be expressed, but cannot be identified with certainty. If $\Delta S(A)$ is empty, the solution is unique.

Having a set $\Delta S(A)$ of ambiguous targets does not mean that expression levels cannot be determined correctly. It may be possible to distinguish them due to the fact that the numerical value of the expression levels is different for different targets. An algorithm for determining these is considered below.

The computation of the array D(A) and the set S(A) can be accomplished simultaneously by the following modification of Algorithm 1. Assume the initial construction of a database of indices $l^g_1, \ldots, l^g_k$ of all indices such that $P(g)_{l_i^g} = 1$ for all $g \in U$. Note that this can be done computationally based on knowledge of the complementary matches between targets and probes and does not require experimental determination.

Algorithm 2 Set all array values of D(A) to zero. Loop over all $g \in U$. For all i such that $P(g)_{l_i} = 1$, test whether or not $A_{l_i} = 1$. If it is, include g in S(A) and increment $D(A)_{l_i}$.

Once the computation of the array D(A) and the set S(A) is completed, the set $\Delta S(A)$ can be computed by the following algorithm.

Algorithm 3 Loop over all $g \in S(A)$. For all i such that $P(g)_{l_i} = 1$, test whether or not $D_{l_i} \geq 2$. If all of them are, include g in $\Delta S(A)$.

Theorem 4 Algorithm 2 computes the array D(A) defined in (2) in an amount of time that is linearly proportional to the size of the universe of targets U. Algorithm 3 computes $\Delta S(A)$ in an amount of time that is linearly proportional to the size of S(A). The constants of proportionality depend only on the average number of non-zeroes in any P(g).

Simple examples now presented will show how the algorithms presented above work in practice. If there is only one $g \in U$ such that $P(g)_l$ is non-zero for a given array index l, then $A_l \neq 0$ implies that $g \in S(A) \setminus \Delta S(A)$. Since g is unique, it can be referred to as $g_l$. If this holds for all Q, then $\Delta S(A) = \phi$ for any hybridization array A, and the expression determination is always unique. Note that the number of such that $g = g_l$ for a fixed g can be greater than one, which is the polygamous case.

The next most complicated case would be when each hybridization index l has at most two targets g such that $P(g)_l$ is nonzero. For simplicity, also assume that the hybridization array P(g) has exactly two non-zero entries per g. In this case, there is a canonical way to number the targets and the hybridization indices that simplifies the expression presentation and analysis, which is described below.

Select one g and call it $g_1$ and correspondingly number one of the array locations by "1" so that $P(g_1)_1$ is nonzero. Let array index number 2 be the other l such that $P(g_1)_l$ is nonzero. Thus $P(g_1)_i$ is nonzero precisely for i=1, 2. Suppose there is another g such that $P(g)_2$ is non-zero. Call that target number 2. Thus by definition $P(g_2)_2$ is now nonzero. If there is another l such that $P(g_2)_l$ is non-zero, let this be called the 3-rd array index. Continuing in this way, the result is a sequence of targets such that $P(g_j)_i$ is non-zero precisely for i=j, j+1.

Of course the process could terminate in one of two ways. First of all, there may be no other g such that $P(g)_i$ is non-zero, so target i−1 is uniquely identified by the i-th hybridization signal value. In this case, the first i−1 targets can be determined from the first i hybridization signal values. Then numbering can start over with the remaining targets and hybridization signal values following the same algorithm.

In the second case, the second hybridization index l with non-zero $P(g_{j-1})_l$ may be previously numbered, in which case there is a cycle back into the current group. By construction, each hybridization index i>1 already has two targets g (precisely $g_i$ and $g_{i-1}$) with non-zero hybridization signal values. Since the assumption is that there are at most two targets g such that $P(g)_l$ is non-zero, when a non-zero $P(g_{i-j})_l$ is found which is previously numbered, it must be l=1. Again, the algorithm can be started over with a new g to form a new group. By the assumption on the bound of at most two targets per hybridization signal value, these groups will all be disjoint. This means that the matrix $P_{ij}=P(g_j)_i$ is a lower bi-diagonal matrix, except for an occasional "loop back" entry.

Note that array values and targets are numbered using the same numerical values such that $P_{ij}$ is non-zero for just j=i, i+1 in the generic case. For simplicity, consider hybridization array data A that is zero at the beginning and end of each group as defined above. Then it is easy to identify which parts of U are in S(A) and ΔS(A). The hybridization array A is made up of a number of connected intervals [i, i+k] in which the hybridization values are non-zero, with zero values in between. The interval boundaries identify the targets in the set S(A)\ΔS(A), since they can be determined uniquely. However, the targets corresponding to interval interiors must be in ΔS(A). Thus, whenever there is an interval of three or more consecutive non zero hybridization values, there will be non-determinism in the expression pattern. As discussed below, (non-binary) hybridization signal levels can disambiguate these expression patterns Consider the situation in which the individual expression levels are not just binary values. Suppose that a probe array has a digital output presented as an array $A=(A_l)$ of hybridization signal values, which are non-negative numbers. Similarly, particular targets g will cause a certain hybridization array P(g) to occur. P(g) is an array of hybridization levels indexed by l, each entry $P(g)_l$ a non-negative number. It would be a reasonable assumption that the non-zero values $P(g)_l$ might have the same magnitude for all l. However, this appears not to be the case in some situations [7][8].

In particular, it is quite reasonable to assume that P(g) will have nonzero values corresponding to hybridizations with base-pair mismatches. Hybridization kinetics for oligos is well understood in solution [3][16], but the details of hybridization at surfaces remains a problem of interest. The approach presented here allows expression determination even in the case when complex hybridization occurs.

The expression determination problem can then be described as follows:

Determine a set $\{e_g \geq 0 : g \in U\}$ of target expression values defined by $$\sum_{g \in U} e_g P(g)_l = A_l \forall l. \quad (4)$$

Using vector and matrix notation, this can be simplified. Define P to be the matrix indexed by array indices l and by g∈U with value $P(g)_l$. That is $$P_{l,g}=P(g)_l \quad (5)$$

Define E to be a vector with components $e_g$ indexed by g∈U. Then the expression determination problem is as follows:

Find a vector E of gene expression values defined by "solving"

$$PE=A, E \geq 0 \quad (6)$$

where E≥0 means that $e_g \geq 0$ for all g∈U.

Unfortunately, there need be no "solution" to (6) for arbitrary arrays A≥0 due to the positivity constraint, E≥0. The domain space (e.g., the set of possible E's) of the matrix P is the size n of the set U, and the range or image set (e.g., the set of possible A's) is of size k of the array. In the polygamous approach discussed earlier, k>>n, meaning that the system PE=A is an over-determined system. A necessary condition for solutions to PE=A to exist is that A be in the range of P, and this corresponds to k−n constraints which must be satisfied.

There is a simple restriction on the matrix P that will occur later, but described now for clarity. If a column of P is identically zero, say the column indexed by a particular g∈U, then this would mean that $P(g)_l=0$ for all l, which in turn means that there is no probe that identifies g. Clearly this means that predictions about expression levels of g can not be made. In some sense, this would mean that g is not in the "universe" of targets that can be probed. Thus, a natural condition to impose on P (or more precisely, on the "universe" U) is that no column of P is identically zero.

In the promiscuous approach discussed earlier, it is reasonable to assume that n>>k. This means that the system PE=A is an under-determined system. A sufficient condition for solutions to PE=A to exist is that P has full rank. The set of solutions to PE=A is either empty or else an affine set of high dimension (dimension n−k in the case of P full rank, even higher when P is rank deficient). It is possible that none of the elements of this set satisfy the constraint E≥0. The following algorithm does not assume that P has full rank; solutions in this case exist only for data satisfying constraints similar to those in the over-determined case.

A preferred method of the present invention is based on linear programming (LP) to determine whether the feasibility problem (6) has a solution, and to find such a solution if one exists. The initial linear programming formulation introduces vectors s and t, each containing k artificial variables indexed by l. The formulation is as follows:

$$\min_{E,s,t} \Sigma_l s_l + t_l \text{ subject to} \quad (7)$$

$$(E,s,t) \geq 0, PE+s-t=A. \quad (8)$$

Note several points about this LP. First, given any guess E satisfying E≥0, a feasible starting point can be constructed by setting $$s_l=-\min((PE-A)_l, 0), t_l=\max((PE-A)_l, 0). \quad (9)$$

Second, the objective value is bounded below by 0, because of the constraints that all components of s and t remain nonnegative. Thus the LP is feasible and bounded, and so it has a solution. Third, note that any solution E of the original system (6) can be transformed into a solution of (7-8) by setting s=t=0. Using this fact, a certificate of feasibility for (6) can be obtained by solving (7-8); if the solution of (7-8) results in a strictly positive optimal value, then there exists no solution to (6). On the other hand, if the solution of (7-8) yields an objective value of zero, a solution to (6) is obtained by simply taking the E component of the solution to the LP. Finally, note that no assumptions on P (or k or n) are needed. These facts are collected in the following result.

Theorem 5 For any P and A, the minimization problem (7-8) always has a solution and can be started at the feasible point given by (9) for any E. The minimum value in (7) is zero if and only if the E component of the minimizer is a solution of (6).

One can show that there exists a solution of (7-8) that has at most k nonzeros in the solution vector (E, s, t), and that the simplex method will find such a solution.

If in fact (6) is infeasible, the solution of (7-8) yields a nonnegative vector E for which the inconsistency in the equations PE=A is minimized in the 1-norm.

A reasonable choice for initial E is the array E(A) defined by $E(A)_g=1$ (or a predetermined positive value) if $g \in S(A) \setminus \Delta S(A)$ (see Theorem 7).

FIG. 1 lists the steps in the preferred method for determining a matrix of expression levels corresponding to a set of biological targets and a set of biological sample.

In step 101, a matrix of hybridization values P corresponding to the set of biological targets is obtained.

Next, in step 102, a vector of expression levels for a sample in the set of biological samples using the matrix of hybridization values P is computed.

In step 103, the vector of expression levels computed in the computing step is stored in a storage matrix.

In step 104, if expression levels have been computed for all of the samples in the set of biological samples, the method proceeds to step 105. Otherwise, steps 102 and 103 are repeated.

Finally, in step 105, the storage matrix is outputted as the matrix of expression levels.

Figure 2:
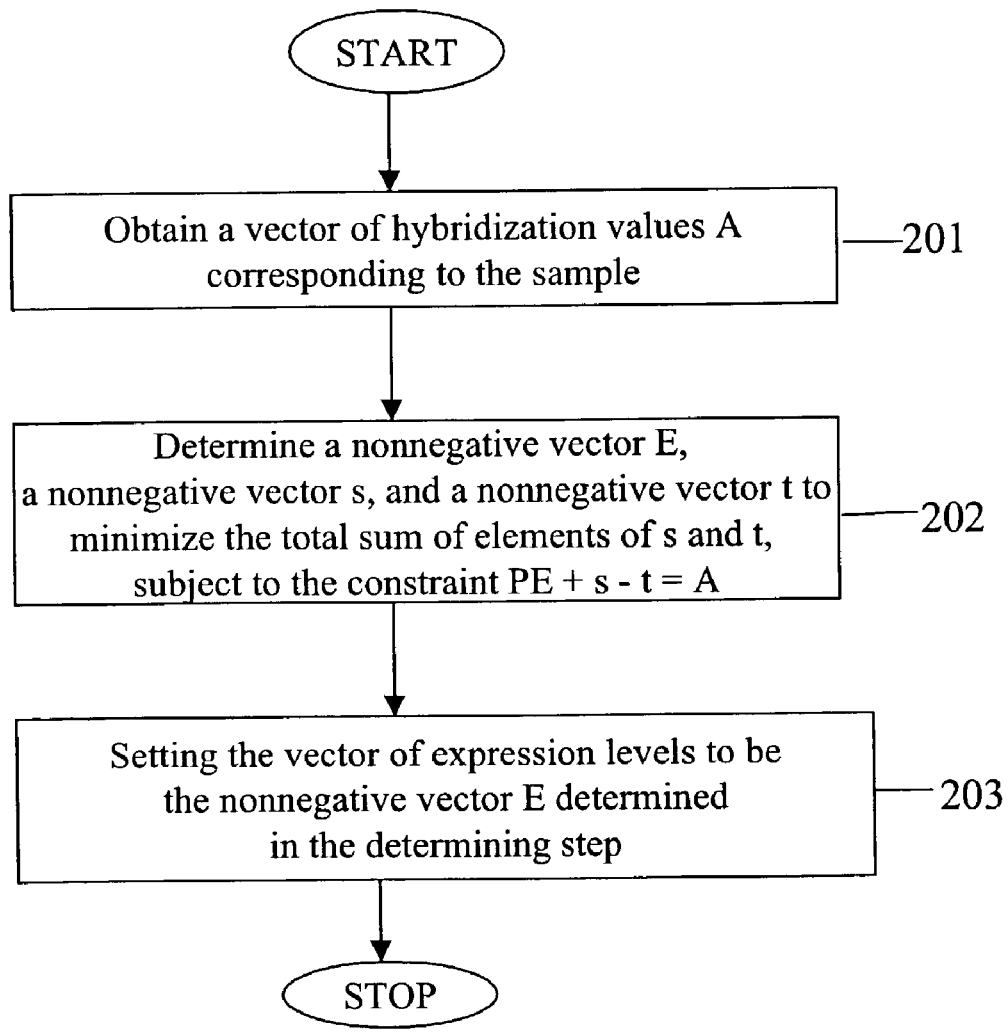
FIG. 2 is a flowchart showing the steps of determining a vector of expression levels for a biological sample according to the first embodiment of the present invention.

FIG. 2 lists the steps in the preferred method for computing the vector of expression levels for a sample in the set of biological samples using the matrix of hybridization values P.

In step 201, a vector of hybridization values A corresponding to the sample is obtained.

Next, in step 202, a nonnegative vector E, a nonnegative vector s, and a nonnegative vector t that minimize a total sum of all elements of s and t, and satisfy a constraint PE+s−t=A are determined. A linear programming algorithm, such as the simplex method, can be used at this step.

Finally, in step 203, the vector of expression levels is set to be the nonnegative vector E determined in step 202.

It is often the case that probes are duplicated on a single biological expression array as a way of detecting hybridization errors. In principle, all duplicate probes should have the same hybridization signal levels, but in practice they do not. Different protocols can be observed to deal with the multiple data. One approach would be to average the values, and another would be to "vote" on the best value. Either of these, or some other method, could be used to define a single hybridization signal value for each probe, and the previous algorithms can be used.

Consider a more general formulation of the problem of determining expression levels, which is applicable when the correct values of some of the components of $A_l$ is uncertain.

Suppose that instead of a precise value $A_l$, there is an interval $[L_l, H_l]$ that contains the value. In other words, accept E as a valid vector of expression levels if $$L_l \leq \sum_{g \in U} e_g P(g)_l \leq H_l.$$

(If the precise value is known, simply set both $L_l$ and $H_l$ equal to $A_l$.) The formulation analogous to (7-8) is then $$\min_{E,s,t} \Sigma_l s_l + t_l \text{ subject to} \quad (10)$$

$$(E, s, t) \geq 0, \ s \geq L-PE, \ t \geq PE-H. \quad (11)$$

This formulation would in general be no more difficult to solve than (7-8).

Figure 3:
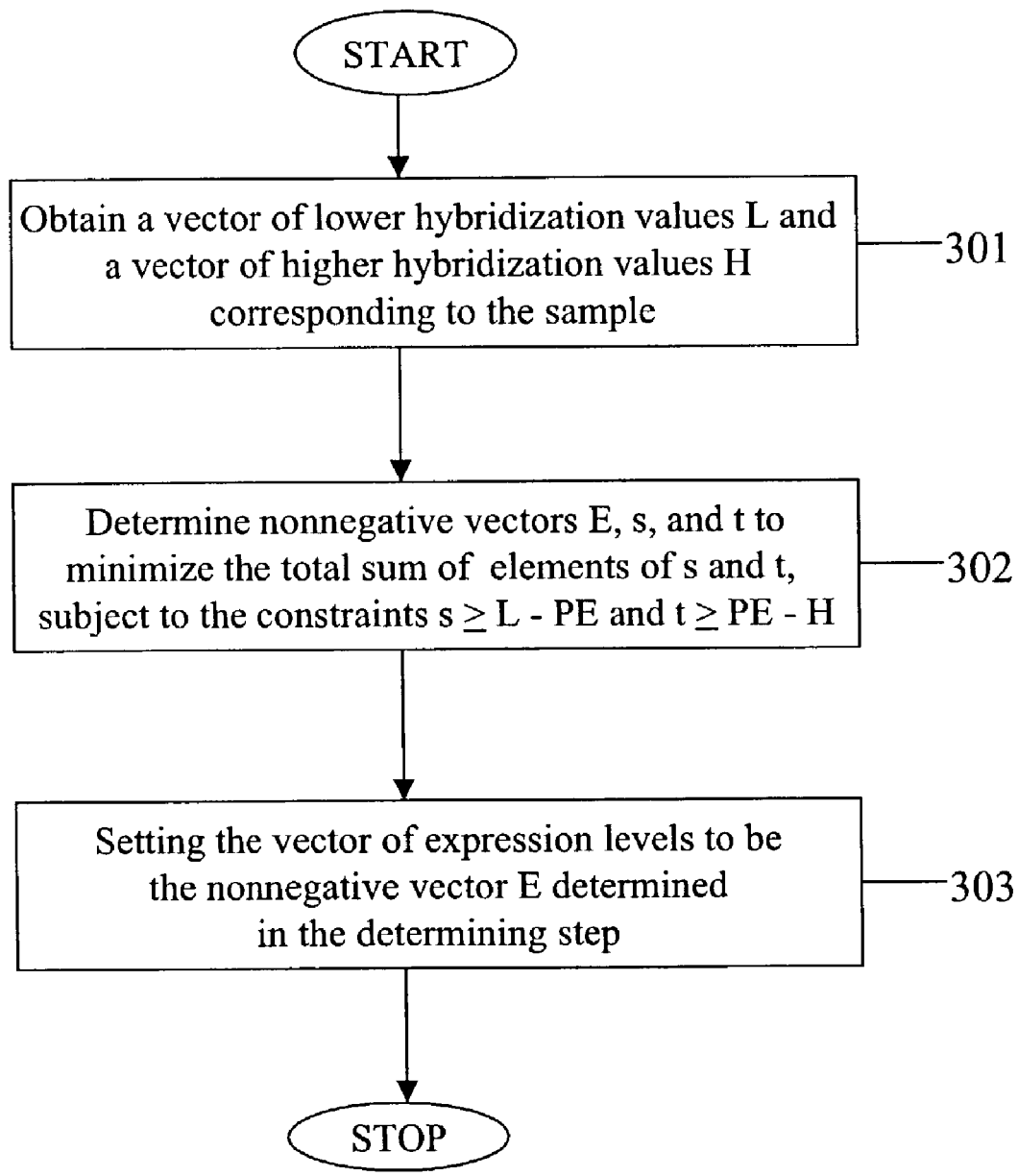
FIG. 3 is a flowchart showing the steps of determining a vector of expression levels for a biological sample according to a second embodiment of the present invention.

FIG. 3 lists the steps in a method for computing the vector of expression levels for a sample in the set of biological samples using the matrix of hybridization values P, according to a second embodiment of the present invention.

In step 301, a vector of lower hybridization values L and a vector of higher hybridization values H is obtained by testing the biological sample with an array of reactive probes, each element of L being less than or equal to a respective element of H.

In step 302, a nonnegative vector E, a nonnegative vector s, and a nonnegative vector t, that minimize a total sum of all elements of s and t, and satisfy constraints s≥L−PE and t≥PE−H are determined. A linear programming algorithm, such as the simplex method, can be used at this step.

Finally, in step 303, the vector of expression levels is set to be the nonnegative vector E determined in step 302.

Returning to the formulation (7), consider the case in which the set (6) is nonempty. As mentioned above, the E component of any solution of (7-8) that has s=t=0 is a member of this set. In general, the set of vectors E satisfying (6) will be a (possibly unbounded) polytope. It may, however, be of interest to obtain some particular solution from the optimal set, or to learn something about the properties of this set.

To begin with, observe that in this case, the set of vectors E satisfying (6) will be a bounded polytope.

Theorem 6 Suppose that the matrix P has non-negative entries and that none of its columns are identically zero. Then the set (6) is bounded.

Proof. The set (6) is unbounded if and only if there is a vector $F=[f_g]_{g \in U}$ such that $$F \geq 0, \ PF=0, \ F \neq 0. \quad (12)$$

Suppose some component $f_g$ of F is strictly positive. By the assumptions, there is an index l such that $P(g)_l$ is strictly positive. The l-th component of PF is at least $P(g)_l f_g$, which is strictly positive, contradicting PF=0. Hence no such component $f_g$ exists, and F=0. Thus, no solution to (12) exists, and hence the set (6) is bounded.

It may be useful to find the solution of minimum-norm in case there exist multiple solutions. One can minimize the 1-norm by solving the following LP:

$$\min \sum_{g \in U} e_g \text{ subject to } E \geq 0, \ PE = A, \quad (13)$$

using the E component of the solution obtained from (7-8) as a feasible starting point for (13). Using a Euclidean norm criterion, one can solve $$\min \frac{1}{2} \sum_{g \in U} e_g^2 \text{ subject to } E \geq 0, PE = A. \quad (14)$$

This is a convex quadratic program [1] rather than a linear program, but it can still be solved with interior-point software (see Chapter 8, "Primal-dual interior-point methods" in *Numerical Optimization* by Nocedal and Wright [15]). Variants of (13) and (14) that use weighted norms or the ∞-norm can be formulated easily.

One could also seek extreme points of the set (6) by solving linear programs with random linear objectives. For instance the problem $$\min \sum_{g \in U} x_g e_g \text{ subject to } E \geq 0, PE = A, \quad (15)$$

where each $x_g$ is a random variable (drawn from some distribution that allows both positive and negative values) will yield a vertex of the optimal polytope. By solving a sequence of problems of the form (15), for different choices of x, one can construct a subset of the optimal polytope by taking the convex hull of the solutions obtained in this process. By inspecting this subset, one may for instance be able to restrict the ambiguity produced by the data to certain subspaces. Noting that certain components $e_g$ of the solution are identical (or nearly identical) regardless of the choice of x, one might conclude that these components are well determined by the data.

There is an intriguing connection between the discrete model (the identification problem) and the continuous (expression-level determination) problem. The sets S and ΔS allow us to determine the active set for the minimization problem of equations (7-8). But first consider modified definitions suitable for the more general expression values being considered here.

Generalizing the definition in equation (1), define $$S = S(A) = \{g \in U : P(g)_l > 0 = > A_l > 0 \forall l\}. \quad (16)$$

The solution S(A) to (16) can still be computed by a simple modification to Algorithm 1. Similarly, equation (2) can be replaced by the more general definition $$D(A)_l = \text{cardinality } \{g \in S(A) : P(g)_l > 0\} \quad (17)$$

while keeping the definition (3) of ΔS(A). These can be computed by simple modifications of Algorithms 2 and 3. With these new definitions, one obtains the following modification of Lemma 1.

Lemma 2 For any $g \in S(A) \backslash \Delta S(A)$ there is at least one array index $l_g$ such that $P(g)_{l_g} > 0$ and for all other $g' \in S(A)$ (with $g \neq g'$), $P(g')_{l_g} > 0$.

Using this Lemma, one can now prove the following result which characterizes the active set for a minimization problem for solving (6). Note that the solution (E, s, t) to (7-8) satisfies PE=A=A−s+t.

Theorem 7 Suppose there exists an expression level vector E such that $$PE = A, E \geq 0. \quad (18)$$

Then $$S(A) \backslash \Delta S(A) \subset \{g \in U | e_g > 0\} \subset S(A). \quad (19)$$

Proof. Consider first the right inclusion in (19). Suppose for contradiction that $e_f > 0$ for some $f \in U \backslash S(A)$. Then by definition of S(A) there exists an index k such that $$P(f)_k > 0 \text{ and } A_k = 0.$$

From (18), it follows that $$0 = A_k = \sum_{h \in U} P(h)_k e_h \geq P(f)_k e_f > 0,$$

giving the desired contradiction.

To prove the left inclusion in (19), take an arbitrary $g \in S(A) \backslash \Delta S(A)$ and try to show that $e_g > 0$. By Lemma 2, there is an index l such that $$P(g)_l > 0, \text{ while } P(h)_l = 0 \text{ for all } h \in S(A) \backslash \{g\}. \quad (20)$$

In particular, since $g \in S(A)$, it follows from (16) that $$A_l > 0. \quad (21)$$

In addition, it is true that $e_h = 0$ for all $h \in U \backslash S(A)$, by the argument above. By (18) and (20), it follows that for this index l $$0 < A_l = \sum_{h \in U} P(h)_l e_h$$

$$= P(g)_l e_g + \sum_{h \in S(A) \backslash \{g\}} P(h)_l e_h + \sum_{h \in U \backslash S(A)} P(h)_l e_h$$

$$= P(g)_l e_g.$$

Therefore $e_g > 0$ as required, proving the result.

This result says that, if there is a solution to (6), then any algorithm for finding it may be restricted by assuming that $e_g = 0$ for $g \notin S(A)$. That is, compute S(A) first, and then start looking for a solution E "supported" in S(A). Moreover, one can be sure that all $e_g$ are positive for $g \in S(A) \backslash \Delta S(A)$. For example, restrict the minimization problem in equations (7-8) to $E \in S(A)$ only.

One question of interest is what the linear programming model does when there is a hybridization array that relates to a target expression pattern for a target not in the universe U. Suppose that there is some $g \notin U$ with hybridization pattern B=P(g). If there is an hybridization pattern A°=PE° perturbed by adding B to get an hybridization pattern A=A°+B, then the linear programming model (7-8) will produce an answer (E, s, t) with $$PE + s - t = A = A° + B = PE° + B. \quad (22)$$

Thus the error E−E° satisfies the error equation $$P(E - E°) = B - s + t. \quad (23)$$

Similarly, it is useful to know what the linear programming model will produce if there is a perturbation, e.g., due to noise. But the formulation reduces to the same considerations in which B is interpreted as a perturbation due to noise.

The algorithm of equations (7-8) is a minimization problem, and the vector (E°, s°, t°) is a feasible approximant, where s°−t°=B, that is $$s°_l = \max(B_l, 0), \quad t°_l = -\min(B_l, 0). \quad (24)$$

Note that $$PE° + s° - t° = A° + s° - t° = A° + B = A. \quad (25)$$

By the optimality condition of (7-8)

$$\|(s, t)\|_{l^1} \leq \|(s°, t°)\|_{l^1} = \|B\|_{l^1}. \quad (26)$$

Thus the role of s and t can be interpreted as making the hybridization A=A°+B−s+t satisfy the implicit constraint needed so that the system (6) has a solution E≧0 with right hand side A. One bound on the size of s and t is that s and t need be no bigger than required simply to cancel B completely, but s and t can be smaller as well. Thus s and t provide a lower bound for the size of the (unknown) perturbation B.

In the case that the matrix P is invertible, this means that whatever the perturbation B there will be a unique expression E attributed to it. The only indicator of error is the size of s and t.

The lower bound (26) means that the size of $\|(s, t)\|_{l^1}$ is a conservative estimation of the size of the hybridization error. Thus it may underestimate the error, but it will never overestimate it. Otherwise said, if it is large, then there is definitely a large discrepancy in the data, and it should not be trusted.

Recall that the error E−E° satisfies the error equation (23), namely, P(E−E°)=B−s+t. But then (26) implies that $$\|B-s+t\|_{l^1} \leq \|(s, t)\|_{l^1} + \|B\|_{l^1} \leq 2\|B\|_{l^1}. \quad (27)$$

In the case that P is invertible, this allows us to give a bound on the expression error E−E°.

Previously, two examples of possible expression array matrices were presented. In the first example there is only one g∈U such that P(g)$_l$ is non-zero for a given array index l, which is referred to as $g_l$. One can number the targets and probes in such a way that the expression matrix P$_{i,j}$=P(j)$_i$ has a simple form. Let the first target index j=1 correspond to some g∈U for which P(g)$_l$ is non-zero for some l. There is some number $I_1 \geq 1$ of array indices l such that P(g)$_l$ is non-zero. Number these array indices 1, . . . , $I_1$. Now pick another g∈U for which P(g)$_l$ is non-zero for $I_2 \geq 1$ array indices l, and call this target j=2 and number these array indices $I_1+1$, . . . , $I_1+I_2$. Continuing in this fashion, one constructs a matrix P with only one non-zero per row, such that the j-th column consists of $I_1+I_2+\ldots I_{j-1}$ zeros, followed by $I_j$ non-zeros, and then followed by all zeros. For simplicity, assume that all the non-zeros are ones.

As shown above, expression determination is always unique in this case. However, it is interesting to consider how the algorithm (7-8) deals with this case, especially in the presence of noisy data. The role of the extra variables s and t in this case is to make sure that the hybridization array A−s+t is in the range of the matrix P. The range of P is easy to describe. It consists of vectors A such that the entries $I_j+1$, . . . , $I_{j+1}$ all have the same value, for each j (for completeness, define $I_0=0$). For any A not satisfying this constraint, algorithm (7-8) will adjust the variables s and t to make the vector A−s+t satisfy this property.

It suffices to see what happens with a single block j, so consider the case when P is a k=$I_1$ by 1 matrix (one expression value only, with k hybridization array values). For simplicity, assume that the first k−1 hybridization values of A are α>0 and the k-th value is β≦α. This would correspond to a simple error in one of the hybridization array values. Then it is easy to see that the optimal vectors s and t will have the following form. The first k−1 values of s will be some value σ and the k-th value will be zero. The first k−1 values of t will be zero, and the k-th value will be some value τ. To have A−s+t be in the range of P, it must be true that α−σ=β+τ. Thus $$\Sigma_i(s_i+t_i) = \sigma(k-1) + \tau = \sigma(k-2) + \alpha - \beta. \quad (28)$$

If k>2, this is minimized by taking σ=0 (and so τ=α−β) which corresponds to the expression value obtained by the "voting" algorithm: the consensus k−1>1 values α are confirmed. In the case k=2 (when there is a tie), the resulting solution adjusts the array so that A−s+t corresponds to the average (α+β)/2. Thus the optimization algorithm (7-8) does a very reasonable thing in this case.

When the data is more complex, the effect of the optimization algorithm (7-8) is more complicated to describe. The resulting "consensus value" will be one of the array values, the one that minimizes the $L^1$ norm of the deviation from the other values. FIG. 1 shows how this would work with some synthetically generated random data. As shown in FIG. 1, the algorithm does a good job of "healing" errors introduced by noise.

In the second example above the case in which there are at most two targets g such that P(g)$_l$ is nonzero for any l, and for which there are exactly two non-zero hybridization levels per target was considered. In this case, the expression matrix P$_{i,j}$=P(j)$_i$ is a lower bi-diagonal matrix, except for an occasional "loop back" entry. Each of these "loop backs" marks a block of independent expression, so focus on just one. For simplicity, just assume that P=($p_{ij}$) is of the form $p_{11}=1$, $P_{i,i-1}=P_{i,i}=1$ for all i=2, . . . , n and the rest are zero. Expression analysis in this case is equivalent to solving the equation PE=A, and it is possible to invert the matrix P explicitly. Let Q=($q_{ij}$) be the lower-triangular matrix whose i-th row satisfies $q_{ij}=(-1)^{i-j}$. Then Q is the inverse of P. Thus expression levels can be determined from E=QA, provided these values are non-negative.

One thing this example makes clear is that the ambiguity resulting from ΔS(A)≠φ above, which occurs for any array data with three or more consecutive non-zero values, does not lead to an inability to determine expression levels. Any hybridization array A will yield an unambiguous expression E=QA. Thus utilizing (non-binary) expression levels leads to a more robust identification system.

Having an explicit inverse for P allows one to study the effect of errors in the data. Suppose an array A is perturbed by ∈=(∈$_i$). The resulting expression values are given by Ê=Q(A=∈)=E+Q∈, provided these values are positive. Suppose that ∈$_i$=δ(−1)$^{i-1}$. Then (Q∈)$_i$=δ$_i$. This means that the error can be as large as the number of expression values times the perturbation. Otherwise said, the inverse matrix Q can amplify the error significantly.

One problem with the current approach is the limitation to two non-zero hybridization array locations. It is certainly possible to pick oligos which can target an essentially arbitrary number of genes [4]. There is another simple expression matrix one can examine. Suppose that the i-th probe identifies the first i targets. This corresponds to assuming that $p_{i,j}=1$ for all $j=1, \ldots, i$ for $i=1, \ldots, n$. In this case the inverse matrix Q has the simple form $q_{11}=1$, $q_{i,i-1}=-1$, and $q_{i,i}=1$ for all $i=2, \ldots, n$.

In this example, it is possible to characterize the arrays A for which the corresponding expression levels E are non-negative. The condition $E=QA \geq 0$ can be used inductively as follows. First of all, $0 \leq e_i = \alpha_i$, but this only says that the hybridization array value $\alpha_i$ should not be negative. But for $i>1$, $0 \leq e_i = \alpha_i - \alpha_{i-1}$, and this says that the array values should not decrease in this ordering of the values. This is reasonable since each succeeding value represents more and more targets.

Previously, an analysis of what the linear programming model does when there is an array $A=PE°+B$ for some perturbation B was considered. The algorithm (7-8) produces a solution (E, s, t) where $$PE = A - s + t. \quad (29)$$

Then the role of s and t can be interpreted as making the vector A−s+t satisfy the constraint needed so that $E \geq 0$. In the example, this means that A−s+t must be non-decreasing; recall that A−B=PE° must be non-decreasing to begin with, but there is no reason that A would be.

Consider now the situation when targets in the same experiment have been labeled in different ways, e.g., so the targets appear on the array with different colors. For example, targets could be from different samples: a "normal" sample might be labeled with a green fluorescence label and another sample might be labeled with a red label. If both types of samples are present in equal amounts, the resulting color will appear yellow.

From a mathematical point of view, the expression levels are simply vectors, with one component for each color. Let us assume that there is some number $c \geq 1$ of colors. In the more general, multi-color case, one supposes that the probe array has a digital output presented as an array $A=(A_l)$ of hybridization vectors, where each component $A_l^i$ is a non-negative number, for $i=1, \ldots c$.

Particular targets g will still generate a hybridization array P(g) of scalar hybridization values for each l, again with non-negative components. The color would be determined by the marking, but the response would presumably be the same independent of the marking color, or at least that is the assumption. Let an expression vector $e_g \geq 0$ if $e_g^i \geq 0$ for all $i=1, \ldots, c$.

The multi-color expression determination problem is then as follows:

Determine a set $\{e_g \geq 0 : g \in U\}$ of gene expression vectors defined by "solving"

$$\sum_{g \in U} e_g P(g)_l = A_l \; \forall \, l. \quad (30)$$

Using vector and matrix notation, this can be simplified as before. Define P to be the matrix indexed by array indices l with value $P(g)_l$ and by $g \in U$. Define E to be a vector-valued array indexed by $g \in U$, and define $E \geq 0$ to mean that $e_g \geq 0$ for all $g \in U$. Then the multi-color expression determination problem is as follows:

Determine an array $E \geq 0$ of gene expression vectors defined by "solving"

$$PE = A. \quad (31)$$

This is really just c independent problems, of the form $$PE^i = A^i, \; E^i \geq 0. \quad (32)$$

for $i=1, \ldots c$. Thus the techniques and results discussed above apply. If the original data for the problem is an array A of color values, these will have to be decomposed into constituent colors $A^i$, $i=1, \ldots, c$. But after that, the problem can be solved by techniques developed for the single color case.

Algorithms have been presented based on linear programming that determine expression values from arrays of biological experiments with complex relationships between probes and targets. The algorithms have been analyzed abstractly and bounds have been given to relate certain computed quantities to hybridization error. They have been shown to work for both "promiscuous" array data, in which there may be multiple targets indicated by a single probe, as well as in the "polygamous" case where there are multiple probes for a single target.

In an alternative embodiment, the method for determining biological expression levels can be used with Serial Analysis of Gene Expression (SAGE™) data [4][24][25][27]. In standard SAGE analysis, probes are represented by SAGE tags, n-mer sequences following a given marker sequence, such as CATG. The targets are the genes that contain them. Of course, there can be many such genes [24][4]. Using the notation described above, the corresponding matrix entry $P(g)_l$ is non-zero if the l-th SAGE tag is in the gene (or EST) g, and zero otherwise. For simplicity, one can take the non-zero entries to be equal to one. Multiple matches correspond to a row of P with multiple non-zeros. However, in any given column, there will be at most one non-zero entry. Thus, there is no way to distinguish different expression levels with standard SAGE analysis using the method of the present invention described above.

However, if multiple SAGE analyses are performed with multiple markers (e.g., CTAG, etc.), one can get multiple non-zero entries in columns of P. This provides a set of equations that are amenable to the method of the present invention. Note that there is no concept of mis-hybridization with SAGE (the error rates in sequencing are very small). However, it might be that different markers (CTAG versus CATG) would have different affinity levels, leading to different non-zero coefficients in P. Note that in multi-SAGE analysis, the index l would be different for different markers. That is, CATGAACCGGTTAA (SEQ ID NO:1) is different from CTAGAACCGGTTAA (SEQ ID NO:2). There are potentially sixteen different 4-mer palindromes available to use as markers in multi-SAGE analysis. This would lead to having up to sixteen non-zero elements in each column of the matrix P.

It will be appreciated from the foregoing that the present invention represents a significant advance over other systems and methods for determining biological expression levels. It will also be appreciated that, although a limited number of embodiments of the invention have been described in detail for purposes of illustration, various modifications may be made without departing form the spirit and scope of the invention. Accordingly, the invention should not be limited except as by the appended claims.

The invention claimed is:

1. A computer-implemented method for determining, for a biological sample, a vector of expression levels, each expression level representing a quantity of a target, of a corresponding set of biological targets, that is present in the biological sample, the method comprising:
   obtaining a matrix of signal values P corresponding to the set of biological targets;
   obtaining a vector of signal values A corresponding to the biological sample;
   determining a vector E, a vector s, and a vector t that minimize a sum of all elements of s and t, and satisfy a constraint PE+s−t=A, wherein the elements of the vectors E, s, and t are nonnegative real numbers; and
   outputting the vector E determined in the determining step as the vector of expression levels.

2. The method of claim 1, wherein obtaining the vector of signal values A comprises:
   testing the sample with an array of reactive probes.

3. The method of claim 1, wherein obtaining the vector of signal values A comprises:
   testing the sample with an array of reactive probes,
   at least one probe in the array of reactive probes being indicative of more than one target in the set of biological targets.

4. The method of claim 1, wherein obtaining the vector of signal values A comprises:
   testing the sample with an array of reactive probes,
   each probe in the array of reactive probes being a sequence of oligonucleotides.

5. The method of claim 1, wherein obtaining the vector of signal values A comprises:
   testing the sample with an array of reactive probes including at least one probe which is a sequence of oligonucleotides from at least one part of a known gene.

6. The method of claim 1, wherein the determining step comprises:
   identifying a set of biological targets S(A) consistent with the vector of signal values A; and
   setting, for each target in the set of biological targets that is not in S(A), a respective element of the vector E to zero.

7. The method of claim 1, wherein the determining step comprises:
   using a linear programming algorithm to determine the vector E, the vector s, and the vector t.

8. The method of claim 7, wherein the determining step further comprises:
   constructing a feasible starting point for the linear programming algorithm, for an initial nonnegative vector $E_o$, by initializing an l-th element of the vector s to be $s_l = -\min((PE_o-A)_l, 0)$, and initializing an i-th element of the vector t to be $t_i = -\max((PE_o-A)_i, 0)$.

9. The method of claim 8, wherein the determining step further comprises:
   constructing the initial nonnegative vector $E_o$ by setting each element of $E_o$ to be either zero or, if a corresponding biological target could have uniquely contributed to the vector of signal values A, to a predetermined positive value.

10. The method of claim 1, wherein obtaining the vector of signal values A comprises:
    generating a plurality of short nucleotide sequence tags from the sample;
    concatenating the plurality of short nucleotide sequence tags into a single molecule;
    sequencing the molecule to determine a count for each tag in the plurality of short nucleotide sequence tags; and
    mapping the counts determined in the sequencing step into the vector of signal values A.

11. The method of claim 1, wherein the matrix of signal values P obtained in the obtaining step includes more columns than rows.

12. The method of claim 1, wherein obtaining the matrix of signal values P comprises:
    testing each target in the set of biological targets with an array of reactive probes.

13. The method of claim 1, wherein obtaining the matrix of signal values P comprises:
  testing each target in the set of biological targets with the array of reactive probes, each target being a gene or a gene fragment.

14. The method of claim 1, wherein obtaining the matrix of signal values P comprises:
  generating a plurality of short nucleotide sequence tags for a target in the set of biological targets;
  concatenating the plurality of short nucleotide sequence tags into a single molecule;
  sequencing the molecule to determine a count for each tag in the plurality of short nucleotide sequence tags;
  mapping the counts determined in the sequencing step into the matrix of signal values P; and
  repeating the generating, concatenating, sequencing, and mapping steps for each target in the set of biological targets.

15. The method of claim 1, further comprising:
  storing the vector of expression levels determined in the determining step in a storage matrix;
  repeating the step of obtaining the vector of signal values A, the determining step, and the storing step for at least one biological sample; and
  outputting the storage matrix as a matrix of expression levels.

16. A computer-implemented method for determining, for a biological sample, a vector of expression levels, each expression level representing a quantity of a target, of a corresponding set of biological targets, that is present in the biological sample, the method comprising:
  obtaining a matrix of signal values P corresponding to the set of biological targets;
  obtaining a vector of lower signal values L and a vector of higher signal values H corresponding to the sample, each element of L being less than or equal to a respective element of H;
  determining a vector E, a vector s, and a vector t, that minimize a total sum of all elements of s and t, and satisfy constraints $s \geq L-PE$ and $t \geq PE-H$, wherein the elements of the vectors E, s, and t are nonnegative real numbers; and
  outputting the vector E determined in the determining step as the vector of expression levels.

17. A computer program product comprising a computer storage medium configured to store plural computer program instructions which, when executed by a computer, causes the computer to determine, for a biological sample, a vector of expression levels, each expression level representing a quantity of a target, of a corresponding set of biological targets, that is present in the biological sample, by performing plural steps comprising:
  obtaining a matrix of signal values P corresponding to the set of biological targets;
  obtaining a vector of signal values A corresponding to the biological sample;
  determining a vector E, a vector s, and a vector t that minimize a total sum of all elements of s and t, and satisfy a constraint $PE+s-t=A$, wherein the elements of the vectors E, s, and t are nonnegative real numbers; and
  outputting the vector E determined in the determining step as the vector of expression levels.

* * * * *